US010105535B2

(12) United States Patent
Regnier

(10) Patent No.: US 10,105,535 B2
(45) Date of Patent: Oct. 23, 2018

(54) IMPLANTABLE STIMULATION CAPSULE

(71) Applicant: SORIN CRM SAS, Clamart (FR)

(72) Inventor: Willy M. Regnier, Longjumeau (FR)

(73) Assignee: Sorin CRM SAS, Clamart (FR)

(*) Notice: Subject to any disclaimer, the term of this patent is extended or adjusted under 35 U.S.C. 154(b) by 43 days.

(21) Appl. No.: 15/361,214

(22) Filed: Nov. 25, 2016

(65) Prior Publication Data

US 2017/0151429 A1 Jun. 1, 2017

(30) Foreign Application Priority Data

Nov. 27, 2015 (FR) ...................................... 15 61457

(51) Int. Cl.
*A61N 1/05* (2006.01)
*A61N 1/375* (2006.01)
*A61N 1/372* (2006.01)
*A61B 5/00* (2006.01)
*A61B 5/042* (2006.01)
*A61B 5/07* (2006.01)

(52) U.S. Cl.
CPC ......... *A61N 1/0573* (2013.01); *A61N 1/3756* (2013.01); *A61N 1/37205* (2013.01); *A61B 5/042* (2013.01); *A61B 5/076* (2013.01); *A61B 5/6861* (2013.01); *A61B 5/6882* (2013.01); *A61N 1/0575* (2013.01)

(58) Field of Classification Search
None
See application file for complete search history.

(56) References Cited

U.S. PATENT DOCUMENTS 9,020,611 B2 * 4/2015 Khairkhahan ......... A61N 1/375
607/127
2008/0088397 A1 4/2008 Kretschmer

FOREIGN PATENT DOCUMENTS

| EP | 2 394 695 A1 | 12/2011 |
| EP | 2 818 201 | 12/2014 |
| EP | 2 818 202 | 12/2014 |

* cited by examiner

*Primary Examiner* — Brian T Gedeon
(74) *Attorney, Agent, or Firm* — Foley & Lardner LLP

(57) ABSTRACT

The present disclosure relates to implantable capsules for stimulation. One implantable capsule includes a tubular body and a distal member provided at its distal end with an anchoring device adapted to penetrate into a tissue of a wall of an organ of a patient and a distal electrode, the body accommodating a set of functional elements of the capsule and including a proximal electrode. The capsule includes an electrically insulating member between the body and the distal member to isolate the distal member of said body.

12 Claims, 3 Drawing Sheets

IMPLANTABLE STIMULATION CAPSULE

CROSS-REFERENCE TO RELATED PATENT APPLICATIONS

The present application claims priority to French Patent Application No. 1561457, filed Nov. 27, 2015, which is incorporated herein by reference in its entirety.

FIELD

The present disclosure relates to "active implantable medical devices" as defined by Directive 90/385/EEC of 20 Jun. 1990 of the Council of the European Communities, specifically to implantable devices that continuously monitor heart rhythm and deliver to the heart if necessary pulses of stimulation, resynchronization and/or defibrillation in the event of a rhythm disorder detected by the device.

According to some embodiments, the disclosure relates especially to, but is not limited to, those devices which are in the form of an autonomous capsule for implantation in a heart chamber (atrium or ventricle, right or left). These capsules are devoid of any mechanical connection to an implanted main device (such as the housing of a stimulation pulse generator) or non-implanted main device (external device such as programmer or monitoring device for patient remote monitoring), and are called for this reason "leadless capsules", to distinguish them from electrodes or sensors disposed at the distal end of a conventional catheter (lead), which is traversed throughout its length by one or more conductors galvanically connecting the electrode or the sensor to a generator connected to an opposite, proximal end of the lead.

BACKGROUND

Two categories of autonomous capsules exist. The first category concerns endocardial capsules, which are placed in one of the heart chambers. The second category concerns epicardial capsules which are fixed to the external wall of the myocardium, also known as epicardium.

Endocardial capsules have a cylindrical shape, for example a capsule as shown in FIG. 1 so as to be longitudinally inserted through an in situ implantation accessory, such as a catheter from the venous or arterial system of the patient.

At the end of the capsule a fixing means is present for anchoring the capsule to the desired stimulation site.

An implantable capsule as described in U.S. 2008/0088397 comprises a body housing the main components of the device (electronic circuits, power source, stimulation electrodes, etc.) and a base secured to the body and rigidly supporting means for attachment to the wall, in particular in the endocardial wall.

In the case of cardiac leads, two types of fixation are recognized and traditionally used: the "barbed" fixing is the oldest and is still marginally used, but the leads based on a fixation screw supplanted barbed leads and currently represent majority of the market. They allow a generally robust and effective fixation. The screw has a projecting helical screw which axially extends the body of the capsule and is intended to penetrate into the cardiac tissue by screwing at the implantation site, in the same method as for the conventional screw leads.

However, the fixing of such devices remains a critical issue to the extent that an accidental detachment of the capsule would cause the latter to be released into the heart chamber and then transported by the blood in the venous or arterial system. The complication risk to the patient would be extremely high, and the risk of cardiac system injury that may be generated by the end of the fastening system or any other projecting zones of the implant such as a needle electrode or a projecting ridge.

More than a lead device, an autonomous device meanwhile undergoes stresses and movements generated by the heart wall, as it does not benefit from the axial holding force from the lead body. In addition, it has a certain mass.

To fulfill its permanent anchoring function, the fastening system must also include a function of irreversibility, that is to say, it will only be removed from the heart wall by voluntary intervention of the doctor and according to a predefined procedure, but in no case by repeated movements of the heart.

Additionally, the physician should be able to position the implant and capsule at a location chosen by him, but also to reposition the capsule to another location if the first location does not achieve the expected performance.

Thus, the capsule implant system should be simple and intuitive for the physician, including adoption of implantation procedures close to current practice, which makes use of well known and mastered gestures of the practitioners, including for the implantation of the cardiac leads.

The use of a fixing means comprising an anchoring screw system is in particular described in EP 2818201 (SORIN CRM SAS) and an in situ implantation accessory of such a capsule is disclosed in EP 2818202 (SORIN CRM SAS).

Moreover, these capsules comprise a communication device for communicating with an external device, such as a programmer, by radio frequency or by the human body (HBC) or any other system, and also with one or more other implants, for information transmission and reception.

In order for the capsule, to transmit and receive consistent information, it is necessary that the communication environment is not disturbed, in particular by electric or other fields. In addition to maintaining acceptable lifespan of the capsule after implantation, that is to say about 10 years, the energy cost necessary for communication with an external device should be as small as possible.

Indeed, the energy cost generated by this communication function is significant and must be minimized to ensure maximum longevity of the implant. The link budget between an implant and the peripheral device or devices is paramount to ensure the exchange of data and involves having an electric field as less disturbed as possible and thus link budget with the lowest possible attenuation.

However, it has been observed that the proximity of the metallic fixing means and of the stimulation electrodes causes the formation of an electric field radiation, in particular between first, the attachment means and a first electrode and second, the second electrode.

The electric fields created thereby disrupt communication between the capsule and the external device so as to potentially corrupt the information transmitted between the two devices.

A known solution for reducing the formation of electric fields is to coat the outer surfaces of the fastening means with an insulating coating, for example parylene. However, such a coating with a thickness of about 10 µm does not allow resisting wear due to mechanical movements of the heart. Indeed, during the life of the capsule, namely about 10 years, the capsule will be subjected to approximately 400 million cardiac cycles.

The adhesion of the coating on the fastening means can withstand such mechanical stresses. In addition, cracks in the coating can also be caused by micro-movement of the fixing screw, in particular due to the movement of the heart wall.

Furthermore, it is very difficult to isolate the end of the fastener, this end being pointed in general. Poor insulation of this end results in the generation of leakage current.

Furthermore, the fastening means comprises an anti-unscrewing system having sharp edges, these edges being very difficult to isolate zones.

Finally, a parylene coating has the disadvantage of having a relatively low coefficient of friction which can be detrimental to the attachment system and therefore consequently reduce its effectiveness or result in unscrewing of the capsule.

SUMMARY

The present disclosure aims at providing an implantable autonomous device that avoids the creation of electric fields between the two electrodes.

This is particularly critical, inasmuch as the lifespan of the capsules must be preserved, and it is important to have good communication between the capsule and the external device, to ensure optimum operation of the capsule.

More specifically, the disclosure provides an implantable capsule for this purpose, including an autonomous cardiac stimulation capsule, comprising a tubular body and a distal member having at its distal end an anchoring means suitable for penetrating tissue of a wall of an organ of a patient and a distal electrode, the body accommodating a set of functional elements of the capsule and comprising a proximal electrode.

Typically, the capsule comprises an electrically insulating member between the body and the distal member to isolate the distal member of said body.

According to various advantageous subsidiary characteristics in some embodiments:

The distal member comprises the electrically insulating member.

The anchoring means is secured to the electrically insulating member.

The distal electrode is secured to the electrically insulating member, the electrically insulating member comprising a through hole for electrically connecting the distal electrode to an electrical connection of the body.

The distal electrode and the electrical connection of the body are connected by a conductive member, the electrode is secured to said conductive member by laser firing.

The electrically insulating member has an orifice through which the laser shot is formed.

The body comprises at its distal end, a distal member support, said distal member support comprising an attachment means of the distal member.

The distal support comprises an opening for access to the electrical connection of the body.

The anchoring means of the distal member comprises at least one opening and the distal member comprises at least one pad adapted to be inserted into the orifice of the anchoring means of the distal member.

The anchoring means is secured to an anchoring support secured to the electrically insulating member.

The electrical insulating element comprises a transverse bearing surface in the axis perpendicular to the axis remote from the axis of the capsule and the anchoring support being held by an axle or rod extending in a channel under the transverse bearing surface parallel to the bearing surface.

A method of assembling an implantable capsule such as an autonomous pacemaker capsule is also provided. The capsule comprises a tubular body and a distal member has at its distal end an anchoring means adapted penetrate into a tissue of a wall of an organ of a patient and a distal electrode, the body accommodating a set of functional elements of the capsule and comprising a proximal electrode.

The method can include the following steps:
 a) fixing the anchoring means on an electrical insulating member,
 b) fixing the distal electrode on the electrically insulating member, and
 c) securing the electrically insulating member on the body.

BRIEF DESCRIPTION OF THE DRAWINGS

Further features, characteristics and advantages of the present disclosure will become apparent to a person of ordinary skill in the art from the following detailed description of embodiments of the present disclosure, made with reference to the drawings annexed, in which like reference characters refer to like elements and in which.

DETAILED DESCRIPTION

Embodiments of an implantable capsule will now be described.

Figure 1:
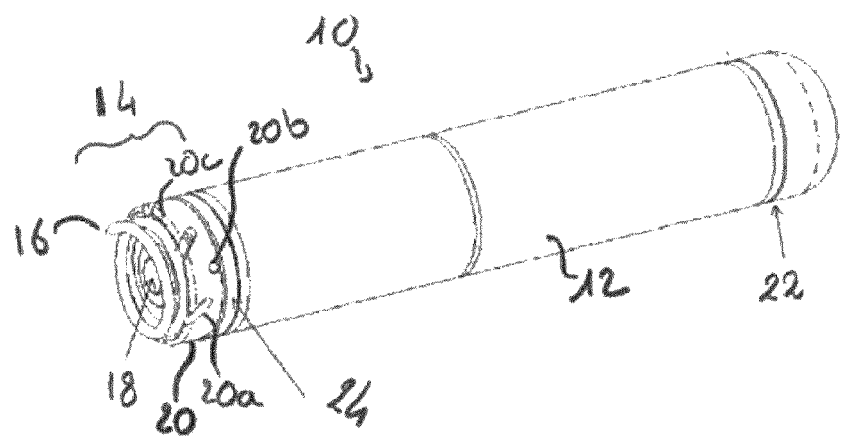
FIG. 1 is an overall perspective view of an implantable capsule according to an embodiment.

Referring firstly to FIG. 1, an implantable capsule 10 is shown, here an autonomous cardiac stimulation capsule, comprising a capsule tubular body 12, a distal member 14 provided at its distal end with anchoring means 16, for example an helical screw and a distal electrode 18.

The anchoring means 16 is a screw is formed by a helically wound wire with right screw pitch and is mounted on an anchor bracket 20 integrating arrangements ensuring the irreversibility of the anchoring. The anchoring means 16 is adapted to penetrate into a tissue of a wall of an organ of a patient.

The screw 16 is permanently secured to an anchor bracket 20.

Note that the material of the screw 16 and of the anchor bracket 20 may be the same, for example stainless steel 316 L for the screw 16 and the anchor bracket 20.

Alternatively, the materials of the screw and of its anchor bracket can be different for example a couple platinum/iridium 90/10 for the screw and titanium for the anchor bracket.

The body of the capsule 12 includes a set of functional elements of the capsule, in particular an electronic module, a battery and also includes a proximal electrode 22.

According to the illustrated embodiment, the capsule comprises an electrically insulating member 24 between the capsule body 12 and the distal member 14 to electrically isolate the distal member 14 of said body 12.

In this method, the distal member 14, including the electrode 18 and the anchoring means 16, is electrically rendered floating relative to the body of the capsule 12. The dipole creation is thus avoided.

According to a particular embodiment, the electrically insulating member 24 is an autonomous element, separate from the capsule body 12 and of the distal member 14.

According to another embodiment, the distal member 14 comprises the electrically insulating member 24.

In yet another embodiment, the capsule body 12 comprises the insulating element 24.

The electrical insulation element 24, due to its proximity to the heart wall, implies that the building material of this element is made of biocompatible material, in particular plastic. The material is for example polyetheretherketone (PEEK Polyetheretherketone), a material used in particular for surgical prostheses elements.

In addition, the electrically insulating member 24 should be resistant to be able to resist the movements of the cardiac implant and the accelerations of the heart.

Figure 2:
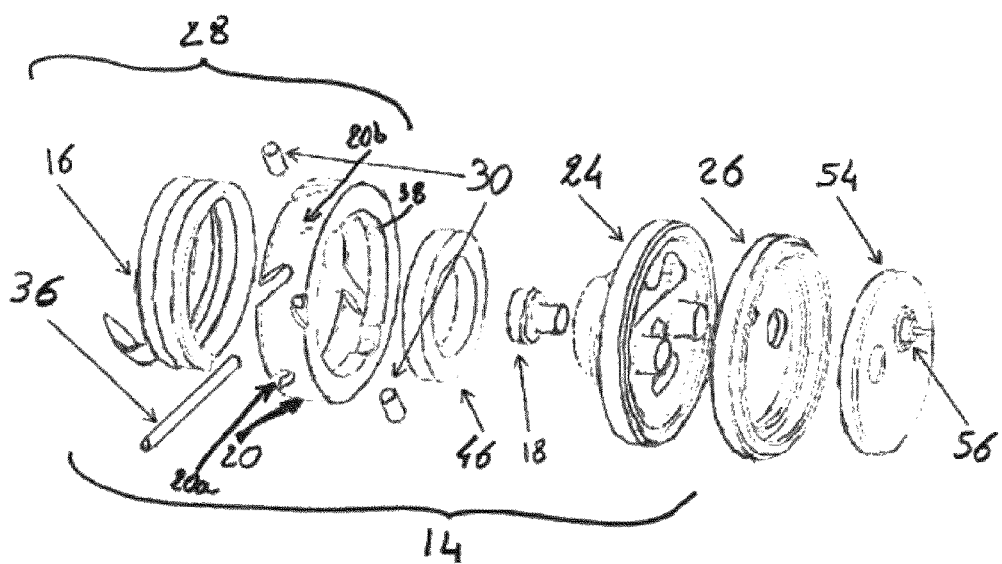
FIG. 2 is a detailed view of the various elements forming the distal member and the support of the distal member in accordance with an embodiment.

FIG. 2 illustrates the distal member 14 and the grip support 26 of the distal element on the body 12.

The distal member 14 of the capsule includes an anchoring subset 28 formed for example of an anchoring means 16 and an anchor bracket 20. This subassembly 28 comprises anchoring facilities to allow irreversible fixation of the anchoring means 16 on the grip wall of the capsule. These facilities include notches or recesses 20a formed in the anchor bracket 20.

The anchoring subset 28 consisting of parts 16 and 20 has a diameter preferably equal to that of the body of the implant, typically 6 to 7 mm, and a slightly smaller axial length, typically between 4 and 6 mm. The anchoring means 16 delimits a space partly occupied by the distal stimulation electrode 18.

The anchoring subset 28 is designed to secure the implant in a stable and sustainable manner over time, through an anchoring means 16, for example a helical screw forming a scalable coil spring and ending with a tip suitable for perforating the endothelium and for penetrating into muscle tissue, so as to press the heart wall about the generally annular end face of the anchor bracket 20, substantially in the same position (in the axial direction) than the inner bearing surface of the electrode system.

In more detail, the anchor bracket 20 presents on said end face a series of recesses 20a which perform the function of irreversibility once in contact with the endothelium. In this position, the fastening system cannot be disassembled: under the action of the screw 16 which acts as a tension spring carrying an axial retaining force, the heart wall is pressed against the face 20c of the anchor bracket 20 and is locally anchored in the recesses by the aforementioned spring effect.

The helix screw 16 is constituted of a metal wire with a diameter of about 0.5 mm, with a winding diameter of typically about 5 mm and preferably equal to or lower than that of the body 12 of the capsule.

The screw comprises a planar base followed by two contiguous turns and a final turn extending, for example about 1.5 turn with an inter-coil space of the same order of magnitude as the diameter of the wire. The free end of the screw 16 is refined, in this case by two machining operations in mutually orthogonal planes, creating a perforating, but not sharp, tip. The purpose of this tip is to cross the endothelium and easily penetrate into the heart muscle while creating minimal tissue damage. The screw 16 is here made of biocompatible implantable stainless steel 316 L or of any other equivalent material which delivers a stiffness of about 0.1 N/mm (linear stiffness of the spring, as measured by tensile or compression using a dynamometer on a 1 mm stroke).

This gives the screw axial flexibility which gives it a spring effect, operating a traction effort to maintain a firm contact between the anchor bracket 20 and the heart wall. Thus, during the penetration of the screw 16 in the muscle, the screw deforms axially until contact of the free edge 20c of the anchor bracket 20 with the endothelium. The spring effect of the screw will then axially compress the endothelium and muscle between the coils and create a wedging effect. In addition, the close proximity of the coils and their traction effect on the endothelium force the entering of the latter in the anti-unscrewing notches 20a. During this movement, the stimulation electrode 18 thus comes into contact with the excitable cells of the heart wall tissue.

The stimulating electrode 18 is, according to an exemplary embodiment, a cylindrical part with the face contacting the dome or plane-shaped heart tissue.

In a particular embodiment, the stimulation electrode 18 is devoid of sharp edges.

Other coils configurations are of course possible, but it is advantageous to provide spacing between the turns which increases from the base of the screw (wherein, as we have seen, the spacing may be zero) and the end of the stimulation electrode. This favors the axial tensile force applying the anchor bracket 20 against the heart wall.

It also understood that the distal electrode 18 is in reliable and continuous contact with the compressed tissues through the axial force of the screw 16 towards the anchor bracket 20.

Such a configuration is particularly suitable for low energy stimulation, with a length of the distal electrode of the order of 1.2 mm and a diameter of the order of 0.4 mm, an active surface of the order of 1 mm².

To firmly hold the anchoring means 16 on the anchor bracket 20, the latter has a configuration comprising a plurality of radial through-holes 20b, having a cross section approximately corresponding to that of stems or spindles 30 and, for example circular, formed in the wall of the anchor bracket 20, these holes receiving homologous stems or spindles 30. The orifices 20b are formed in the anchor bracket 20 at the periphery of the base of the screw 16. In the present example, two through-holes 20b are provided spaced for example by 180°, as well as two corresponding stems or spindles 30. The stems or spindles are made in particular of stainless steel, for example stainless steel 316 L.

The orifices 20b coincide with the part of the screw with contiguous turns. The stems or spindles 30 made of the same material as the screw 16, or of a weldable material to the screw material by laser, is then inserted into each of these side holes.

In the (preferred) case of a spindle, the machining of the spindles leads to the turns of the screw. A laser shot through these holes then enables direct spindle/screw solder ensuring the requirements of a good laser welding, namely: i) material compatibility, ii) direct contact and iii) visual access for shooting and quality inspection.

In a particular embodiment, the anchoring subset 28 is secured to the electrically insulating member 24.

In particular, the anchor bracket 20 is centered on the electrically insulating member 24.

Figure 3A:
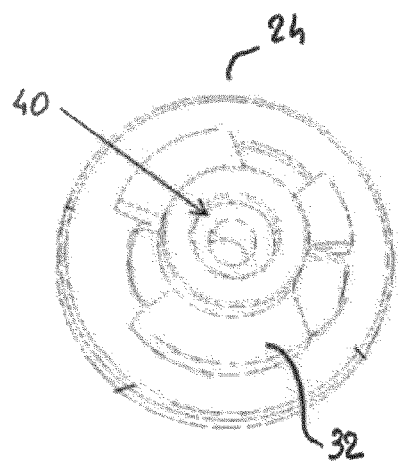
FIGS. 3a and 3b are views of the two faces of the electrically insulating member according to one embodiment.

According to one embodiment, the electrically insulating member 24 comprises, as shown in FIG. 3a, a transverse surface 32 in the axis perpendicular to the axis of the capsule having a given diameter, and serving as bearing surface.

According to an exemplary embodiment, the anchor bracket 20 of cylindrical shape has an inner diameter corresponding to the outer diameter of the transverse bearing surface 32 for securing the anchor bracket 20 to the electrically insulating member 24 by sliding the anchor bracket 20 to the outer periphery of the transverse surface 32 of the electrically insulating member 24.

Figure 4:
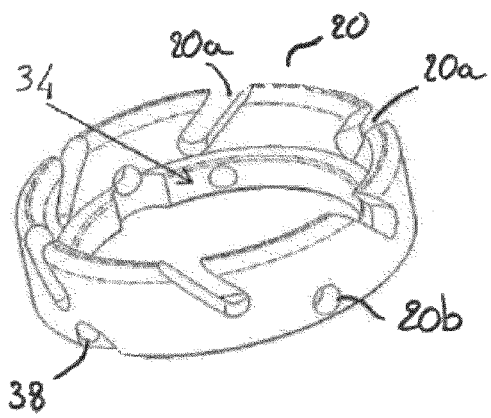
FIG. 4 is a view of the anchoring support according to an embodiment.

According to another embodiment, illustrated in FIG. 4, the anchor bracket 20 includes an inner lip 34 formed at the periphery of the base of anchor bracket at the contact area between the anchor bracket and the electrically insulating member 24, the internal diameter of this lip corresponding to the outer diameter of the transverse bearing surface 32 of the electrically insulating member 24.

According to these embodiments, centering by adjustment of the two parts is thus achieved. In addition, a locking of the two parts along the axis Y and along the axis Z is thus also achieved, as shown in FIG. 2.

A locking of the two parts is also directed along the axis X by inserting a locking pin or a locking spindle 36 in the anchor bracket 20, in particular in individual holes 38 shown in FIG. 2 and in FIG. 4 formed on the periphery of the base of the anchor bracket, on the side of the anchor bracket. The locking pin or the locking spindle 36 is inserted on first in one of the individual holes 38, and then passes through a channel 39 formed in the electrically insulating member 24 as shown in FIG. 2 and in FIG. 3b, then passes through a second particular opening 38.

The channel 39 is formed in particular in the transverse bearing surface 32 parallel to the support surface and offset from the central axis of the capsule.

The locking pin or locking spindle 36 is secured by welding, for example by laser welding at both ends of the spindle on the anchor bracket 20.

Figure 5:
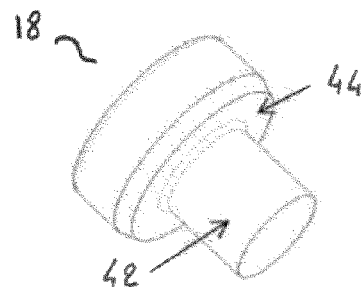
FIG. 5 is a view of the distal electrode according to an embodiment.

As shown in FIG. 2 and in FIG. 3a, the electrical insulator member 24 includes a through orifice 40, for example positioned substantially at the central axis of the capsule, for fixing the distal electrode 18 on the electrically insulating member 24. This orifice is crossing for electrically connecting the distal electrode 18 to an electrical connection of the body of the capsule. The distal electrode 18 illustrated in FIG. 5 comprises a first portion 42 adapted to be inserted into the through hole 40 of the electrically insulating member 24, the first part 42 being of complementary shape to the through hole 40 of the electrically insulating member 24.

According to an exemplary embodiment, the through hole 40 and the first portion of the distal electrode are of cylindrical shape.

The distal electrode 18 comprises a second part 44 adapted to come into contact with the tissue to be stimulated. According to a particular example, the second portion of the distal electrode has a cylindrical shape of diameter greater than that of the first part, in particular to block in depth insertion of the distal electrode 18 in the orifice 40 of the electrical insulation member 24.

The distal electrode 18 is for example fixed to the electrically insulating member 24 by bonding, in particular by means of a biocompatible adhesive. Indeed, the adhesive being liable to migrate near the outer contour of the capsule, and therefore to be in contact with the cardiac wall, the adhesive is for example an epoxy adhesive.

The distal electrode 18 is made for example of platinum and iridium and is coated with a titanium nitride coating (TiN).

The installation of such a capsule should help preserve as much as possible tissue on which the capsule is implanted to allow for example an effective cardiac stimulation. Such implantation can cause an inflammation, nay necrosis of tissues and cells at the site of the anchoring of the capsule and result in a degradation of the effectiveness of stimuli and thus the need to increase the stimulation threshold.

According to various embodiments of the disclosure, a solution to reduce such risks is to use steroids in distally of the cardiac leads, including capsules, so that inflammation and fibrosis formation are reduced.

To do this, the distal member comprises a ring 46, for example a silicon ring impregnated with a steroid such as dexamethasone product.

The steroid product can reduce tissue inflammation during the first weeks after implantation.

Figure 3B:
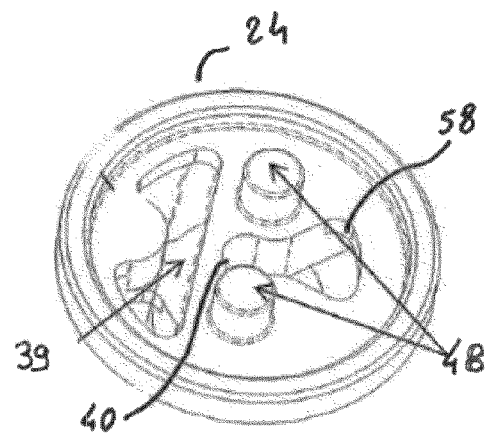

As illustrated in FIG. 2 and in FIG. 3b, the electrical insulation element comprises, on the face opposite the face on which the subassembly anchor 28 and the distal electrode 18 is secured, at least one stud 48, and preferably two studs.

Figure 6A:
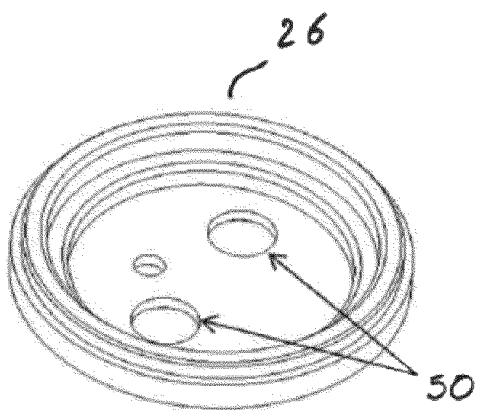
FIGS. 6a and 6b are views of the two faces of the distal support member according to an embodiment.
Figure 6B:
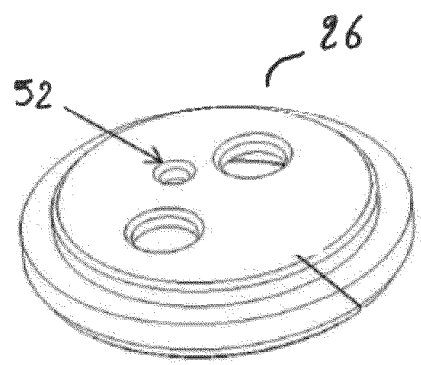

The capsule body 12 comprises at its distal end, an anchor bracket, also known as distal support member 26 shown in FIG. 2 and in FIGS. 6a and 6b. The distal support member 26 is made for example of titanium. This distal support member 26 includes at least one attachment means of the distal member 50.

According to a particular embodiment, the attachment means of the distal member includes one or more openings 50, the stud or studs 48 of the electrically insulating member 24 being capable of being inserted respectively in the holes 50 of the attachment means of the distal member.

The stud or studs 48 of the electrically insulating member 24 and of the orifices 50 of the distal support member 26 are complementary in shape and are adjusted. For example the shape of the studs 48 and holes 50 is round, square or star-shaped.

The assembly of the electrically insulating member 24 and of the distal support member 26 is such that it prevents any rotation between these two parts.

According to one embodiment, a locking of these two parts can be achieved. For example, to lock the axial translation of the stud or studs 48, a deformation step of the material of the studs, for example, cylinders forming pads, is performed to permanently and non-dismountably block these studs in their respective orifices.

Complementary or alternatively, the electrically insulating member 24 and the distal support member 26 may be glued together, in particular with a biocompatible adhesive, for example epoxy. Such bonding has the advantage to fill the interstices present between the two parts during assembly and also to strengthen the assembly.

The distal member support 26 also comprises an additional, relatively narrow, orifice 52 especially of smaller diameter than the orifice studs of the docking ports of the electrically insulating member.

The body 12 of the capsule in its distal part comprises a closing element 54 suitable for closing the body of the capsule, in particular sealingly. This closing element 54 fixed to the body of the capsule comprises a through hole 56 into which a conductive element, from the internal electronics of the capsule housed in the body 12, is inserted. The conductive element is for example a conductive wire.

The electronics associated to the electrodes allows implementing, in the case of cardiac pacing, functions of detection and stimulation.

The conducting wire is guided in the additional orifice 52 of the distal support member 26 to then be attached to the distal electrode 18 on the side of the face of the electrically insulating member 24 bearing one or several studs 48 to be inserted in the distal element member 26.

The conductor wire includes an insulator, such as a heat shrink of PET (polyethylene terephthalate) to prevent short circuits.

The electrically insulating member 24 includes an orifice 58 having a window shape shown in FIG. 3b for welding the electrical wire at the end of the distal electrode 18, for example by means of a laser shot.

According to one embodiment the through-hole 40 and the orifice 58 forming a window constitute a same orifice.

According to some embodiments, the body 12 of the capsule can be coated with a polymer tube such as thermo retracted PET (polyethylene terephthalate) or by a Parylene C micro-coating to isolate the body of the capsule. This insulation is for example positioned on the central body made of titanium and extends from the electrically insulating member 24 up to about 1 mm from the proximal face of the capsule to let a ring of about 20 mm$^2$ emerge, constituting the proximal electrode 22. The dipole thus formed is distant of about a 25 mm length. The length of the proximal electrode can be varied from 1 to 5 mm and thus have a surface of 20 to 100 mm$^2$.

According to some embodiments, the capsule as described above has impedance of approximately 418 Ω and electric field radiation of a value of about 159 mV/m.

An assembly solution of the distal member 14 and its assembly with the distal support member 26 and with the closure member 54 of the body 12 of the capsule will now be described.

The problem solved by this solution is to make the anchoring subassembly 28 electrically floating from the rest of the capsule.

Other significant advantages of this solution, according to some embodiments, are the small footprint and very low complexity of the electrically insulating member 24 to manufacture, including the fact that this element 24 is made of plastic. Such an element can be produced for example by injection molding. The electrical insulation member 24 allows reducing the radiation and the efficiency of electric field created between the distal electrode and the proximal electrode.

According to some embodiments, the assembly method of the capsule preferably comprises the following steps:
a) fixing the anchoring means 16 of an electrically insulating element 24,
b) fixing the distal electrode 18 on the electrically insulating member 24, and
c) securing the electrically insulating member 24 on the body 12.

In detail, the assembly method described above comprises the following substeps, in some embodiments:
1) Production of the assembly of the anchoring means 16 of the anchor bracket 20 by engaging the anchoring means within the anchor bracket 20 and engaging a set of rods or pins 30 in holes 20b present in the periphery of the anchor bracket 20, and welding of stems or spindles 30 on the anchor bracket 20, for example by laser shot,
2) Production of the assembly of the distal support member 26 with the closure member 54 of the capsule body, by engagement of the closure member 54 of the body inside the distal support member 26. This step is carried out for example by stamping and/or by bonding of the two parts, for example with polyurethane adhesive and/or other adhesive.
3) Installation of the conductor element on the closure member 54 of the capsule body by inserting the conductive member into the orifice 52 provided for this purpose and by welding, in particular by laser welding, of the conductor element on the closure member 54 of the capsule body.
4) Insertion of the distal electrode 18 in the orifice 40 of the electrically insulating member 24, on the opposite side to the assembly of the distal support member. The distal electrode 18 is glued into the hole 40 of the electrically insulating member 24, for example by means of a polyurethane adhesive or a biocompatible Epoxy glue, and the conductive member is fixed to the electrode 18 by welding, for example by laser shot applied through the window-shaped hole 58 of the electrically insulating member 24.
5) Assembly of the anchor bracket 20 provided with an anchoring means 16 on the electrically insulating member 24 by engagement of the electrically insulating member 24 in the anchor bracket 20, in particular by engagement of the transverse bearing surface 32 of the electrically insulating member 24 within the anchor bracket 20 and by welding of the locking spindle 36 with the anchor bracket 20. The axial locking and rotation of the anchoring sub-assembly 28 with the electrically insulating member 24 are carried by the locking spindle 36 passing through the channel 39.
6) Fixing of ring 46 (steroid collar) on the transverse bearing surface 32 by means of an adhesive, for example silicone glue.

Note that the "welding" of the steps described above should not be understood in the narrow sense of a mechanical welding with melting of the material of two distinct parts, but in the sense of an operation to collapse the material and reinforce atraumatic function by removal of the projecting shapes.

The various components and parts described above may be made by machining or other shaping according to conventional techniques.

The capsule can be placed by the practitioner according to the technique described in particular in EP 2394695 A1, and also extracted using a known technique, the proximal portion 12 of the capsule body being appropriately formed.

What is claimed is:

1. An implantable capsule for cardiac stimulation comprising:
   a tubular body accommodating functional circuitry and comprising a proximal electrode provided at a proximal end of the tubular body;
   a distal member provided at a distal end of the body, the distal member comprising a distal electrode and an anchoring device structured to penetrate a tissue wall of an organ of a patient; and
   an electrically insulating member between the body and the distal member to isolate the distal member, the electrically insulating member comprising a single piece of insulating material.

2. The implantable capsule of claim 1, wherein the distal member comprises the electrically insulating member.

3. The implantable capsule of claim 1, wherein the anchoring device is secured to the electrically insulating member.

4. The implantable capsule of claim 1, wherein the distal electrode is secured to the electrically insulating member, the electrically insulating member comprising a through hole for electrically connecting the distal electrode to an electrical connection of the body.

5. The implantable capsule of claim 4, wherein the distal electrode and the electrical connection of the body are connected by a conductive member, the distal electrode secured to said conductive member by laser shot.

6. The implantable capsule of claim 5, wherein the electrically insulating member has an orifice through which the laser shot is formed.

7. The implantable capsule of claim 1, the body comprising, at its distal end, a distal support member, said distal support member comprising a fastening device of the distal member.

8. The implantable capsule of claim 5, the body comprising, at its distal end, a distal support member, said distal support member comprising a fastening device of the distal member, wherein the distal support member comprises an opening for access to the electrical connection of the body.

9. The implantable capsule of claim 7, wherein the fastening device of the distal member comprises at least one opening and the distal member comprises at least one stud adapted to be inserted into the opening of the fastening device of the distal member.

10. The implantable capsule of claim 1, wherein the anchoring device is fixed to an anchor bracket secured to the electrically insulating member.

11. The implantable capsule of claim 10, wherein the electrically insulating member comprises a transverse bearing surface in an axis perpendicular to an axis remote from an axis of the capsule and the anchor bracket held by an axle or rod extending in a channel under the transverse bearing surface parallel to the bearing surface.

12. A method of assembling an implantable capsule for providing stimulation, said capsule comprising a tubular body and a distal member having at its distal end an anchoring device adapted to penetrate into a tissue of a wall of an organ of a patient and a distal electrode provided at the distal end of the tubular body, the body accommodating functional circuitry and comprising a proximal electrode provided at a proximal end of the tubular body, wherein the method comprises:
   a) attaching the anchoring device on an electrically insulating member, the electrically insulating member comprising a single piece of insulating material;
   b) securing the distal electrode on the electrically insulating member; and
   c) securing the electrically insulating member on the body.

* * * * *